(12) United States Patent
Vogtmeier et al.

(10) Patent No.: US 12,389,516 B2
(45) Date of Patent: Aug. 12, 2025

(54) DYNAMIC IMAGING SYSTEM WORKFLOW OPTIMIZATION

(71) Applicant: KONINKLIJKE PHILIPS N.V., Eindhoven (NL)

(72) Inventors: Gereon Vogtmeier, Aachen (DE); Paulus René Maria Van Beers, Eindhoven (NL); Dikshit Msr, Pune (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 18/721,903

(22) PCT Filed: Dec. 16, 2022

(86) PCT No.: PCT/EP2022/086335
§ 371 (c)(1),
(2) Date: Jun. 20, 2024

(87) PCT Pub. No.: WO2023/117751
PCT Pub. Date: Jun. 29, 2023

(65) Prior Publication Data
US 2024/0422887 A1 Dec. 19, 2024

(30) Foreign Application Priority Data
Dec. 23, 2021 (IN) .............................. 202141060379
Jan. 14, 2022 (EP) .................................... 22151508

(51) Int. Cl.
H05G 1/36 (2006.01)
A61B 6/00 (2024.01)
(Continued)

(52) U.S. Cl.
CPC ................. *H05G 1/36* (2013.01); *A61B 6/54* (2013.01); *G16H 30/20* (2018.01); *G16H 40/20* (2018.01); *H05G 1/54* (2013.01)

(58) Field of Classification Search
CPC ....... A61B 6/032; A61B 6/4021; A61B 6/545; A61B 6/542; A61B 6/5282; A61B 6/4488;
(Continued)

(56) References Cited

U.S. PATENT DOCUMENTS 6,088,425 A 7/2000 Ono
7,062,016 B2 6/2006 Kawabuchi
(Continued)

FOREIGN PATENT DOCUMENTS

JP 2005058284 A 3/2005
JP 2005243469 A 9/2005
JP 2006294450 A 10/2006

OTHER PUBLICATIONS

PCT International Search Report, International application No. PCT/EP2022/086335, Mar. 30, 2023.

*Primary Examiner* — Irakli Kiknadze
(74) *Attorney, Agent, or Firm* — Larry Liberchuk

(57) ABSTRACT

The present invention relates to X-ray imaging. In order to improve the throughout of an X-ray imaging system, an apparatus is provided for managing an imaging workflow of an X-ray imaging system for an upcoming imaging sequence. The apparatus comprises an input unit, a processing unit, and an output unit. The input unit is configured to receive data including (i) a current temperature profile of an X-ray anode inside a tube housing of the X-ray imaging system, (ii) information about a heat capability and a cooling rate of the X-ray anode, (iii) information about a heat
(Continued)

capability and a cooling rate of the tube housing, (iv) information about a current operation condition of the X-ray imaging system, and (v) information about a planned operation condition of the X-ray imaging system for the upcoming imaging sequence, wherein the planned operation condition comprises a sequence of planned scans, each planned scan being associated with a respective set of planned scan parameters. The processing unit is configured to determine, based on the received data, an estimated temperature profile of the X-ray anode under the planned operation condition for the upcoming imaging sequence. The processing unit is configured to compare the estimated temperature profile of the X-ray anode with a maximum allowable hardware temperature of the X-ray anode. In response to the determination that the estimated temperature profile is greater than or equal to the maximum allowable hardware temperature of the X-ray anode, the processing unit is configured to modify the planned operation condition such that the estimated temperature profile of the X-ray anode under the modified planned operation condition is less than the maximum allowable hardware temperature of the X-ray anode. The modified planned operation condition comprises a change of the sequence of planned scans and/or a change of the set of planned scan parameters for one or more planned scans. The output unit is configured to provide the modified planned operation condition for the upcoming imaging sequence.

14 Claims, 3 Drawing Sheets

(51) Int. Cl.
*G16H 30/20* (2018.01)
*G16H 40/20* (2018.01)
*H05G 1/54* (2006.01)

(58) Field of Classification Search
CPC ....... A61B 6/583; A61B 6/4035; A61B 6/482; A61B 6/502; A61B 6/4042; A61B 6/4092; A61B 6/483; A61B 6/4208; A61B 6/06; A61B 6/466; A61B 6/4085; A61B 6/4028; A61B 6/5241; A61B 6/508; A61B 6/4441; A61B 6/035; A61B 6/037; A61B 6/54; H05G 1/66; H05G 1/56; H05G 1/36; H05G 1/26; H05G 1/54; G21K 1/02; G21K 1/10; G21K 2201/062; G21K 1/06; G21K 2207/005; G01N 23/046; G01N 2223/419; G01T 1/00; H01J 2235/08; H01J 2235/068; H01J 35/105; H01J 2235/1279; H01J 2235/1208; H01J 2235/1204; H01J 35/116; G16H 30/20; G16H 40/20
USPC .......................................................... 378/91
See application file for complete search history.

(56) References Cited

U.S. PATENT DOCUMENTS

| | | | |
|---|---|---|---|
| 11,424,095 B1* | 8/2022 | Acimovic | ................ G01T 1/16 |
| 2004/0264628 A1* | 12/2004 | Besson | .................... G21K 1/10 |
| | | | 378/5 |
| 2015/0312999 A1* | 10/2015 | Takahashi | ............ A61B 6/0487 |
| | | | 378/92 |
| 2019/0320994 A1 | 10/2019 | Lemaitre | |
| 2021/0045706 A1 | 2/2021 | Thibault | |

* cited by examiner

DYNAMIC IMAGING SYSTEM WORKFLOW OPTIMIZATION

FIELD OF THE INVENTION

The present invention generally relates to X-ray imaging, and particularly relates to an apparatus and a method for managing an imaging workflow of an X-ray imaging system for an upcoming imaging sequence, to an X-ray imaging system, to a computer program, and to a computer-readable medium.

BACKGROUND OF THE INVENTION

The throughput of a system may be limited either by the organization of the patient flow including preparation, positioning and repeated imaging due to movement artifacts or other disturbing influences. However, in several cases also the throughput may be limited by the system components. For example, in case of several high power imaging scans in a sequence it might happen that the system has to cool down and the patients and staff have to wait before a next scan could be done.

SUMMARY OF THE INVENTION

There may, therefore, be a need to improve the throughput of an X-ray imaging system.

The object of the present invention is solved by the subject-matter of the appended independent claims, wherein further embodiments are incorporated in the dependent claims.

According to a first aspect of the present invention, there is provided an apparatus for managing an imaging workflow of an X-ray imaging system for an upcoming imaging sequence. The apparatus comprises an input unit, a processing unit, and an output unit. The input unit is configured to receive data including (i) a current temperature profile of an X-ray anode inside a tube housing of the X-ray imaging system, (ii) information about a heat capability and a cooling rate of the X-ray anode, (iii) information about a heat capability and a cooling rate of the tube housing, (iv) information about a current operation condition of the X-ray imaging system, and (v) information about a planned operation condition of the X-ray imaging system for the upcoming imaging sequence, wherein the planned operation condition comprises a sequence of planned scans, each planned scan being associated with a respective set of planned scan parameters. The processing unit is configured to determine, based on the received data, an estimated temperature profile of the X-ray anode under the planned operation condition for the upcoming imaging sequence. The processing unit is configured to compare the estimated temperature profile of the X-ray anode with a maximum allowable hardware temperature of the X-ray anode. In response to the determination that the estimated temperature profile is greater than or equal to the maximum allowable hardware temperature of the X-ray anode, the processing unit is configured to modify the planned operation condition such that the estimated temperature profile of the X-ray anode under the modified planned operation condition is less than the maximum allowable hardware temperature of the X-ray anode. The modified planned operation condition comprises a change of the sequence of planned scans and/or a change of the set of planned scan parameters for one or more planned scans. The output unit is configured to provide the modified planned operation condition for the upcoming imaging sequence.

The prediction of the correct temperature of the anode along the focal spot track inside an X-ray tube during operation can have some impact on the lifetime of the tube and also how the system is operated. It is very important to understand the limits before the tube would be damaged or would suffer from reduced lifetime.

Towards this end, the apparatus and method as described herein estimate the future temperature profile of the X-ray anode for the upcoming imaging sequence based on the parameters of operation and the current temperature profile of the X-ray anode. This may be done utilizing a digital twin model or a trained machine learning model. The apparatus and the method then provide a dynamic workflow optimizer for a medical X-ray imaging system including an X-ray tube and a module configured to optimize scan parameters and/or the sequence of optimized scans as an overall throughput optimization technology based on a temperature prediction before operating the actual hardware. The apparatus and method as described herein may provide a real-time prediction of the temperature profile of the X-ray tube for the upcoming imaging sequence and a real-time adaption of the planned operation before operating the actual hardware.

This will be explained in detail hereinafter and in particular with respect to the examples shown in FIGS. 1 and 2.

According to an embodiment of the present invention, the processing unit is configured to compare the estimated temperature profile of the X-ray anode with a predefined threshold, wherein the predefined threshold is less than the maximum allowable hardware temperature of the X-ray anode. In response to the determination that the estimated temperature profile of the X-ray anode is greater than or equal to the predefined threshold, the processing unit is configured to modify the planned operation condition such that the estimated temperature profile of the X-ray anode under the modified planned operation condition is less than the predefined threshold.

The difference between the predefined threshold and the maximum allowable hardware temperature of the X-ray anode defines a safety margin. As an example, the use of a larger safety margin to avoid risky high temperature scans may be used to plan for the sequence of patient scans. This feature could be very beneficial for extending the life of tube by optimizing/customizing the System EPX parameters to usage needs of the customers. In this way, the hardware (e.g. cooling) probably does not have to take care of worst case/extreme conditions which may be also a chance for cost down and more reliable operation and lifetime. This may allow the apparatus to be used as a "lifetime optimizer".

According to an embodiment of the present invention, the processing unit is configured to modify the planned operation condition to provide a plurality of candidate planned operation conditions, each candidate planned operation condition differing from another in the set of planned scan parameters and/or the sequence of planned scans. The processing unit is configured to determine, under each candidate planned operation condition, a respective estimated temperature profile of the X-ray anode. The processing unit is further configured to select a candidate planned operation condition that has a lowest value of the estimated temperature profile of the X-ray anode.

This may be beneficial for extending the life of the tube.

According to an embodiment of the present invention, the modified planned operation condition comprises a sequence of scans alternating between a high power scan and a low power scan such that a heating rate and the cooling rate of the X-ray node can be balanced to come to a substantially constant operation profile.

In this way, in case an exact temperature profile could be predicted then the system could be operated in a more efficient way as high power scans and low power scans could be interfered and the heating rate and cooling rate could be balanced to come to an optimize constant operation profile. Besides a better and more efficient use of the X-ray tube also more homogenous operating conditions could lead to more precise images due to less variation. This may allow the apparatus to be used as an "efficiency optimizer".

According to an embodiment of the present invention, the apparatus is configured to generate, based on the modified planned operation condition, a control file usable for controlling the X-ray imaging system.

This may be beneficial for an autonomous X-ray imaging system.

According to an embodiment of the present invention, the input unit is configured to receive a planned ambient condition for the upcoming imaging sequence. The processing unit in configured to determine the cooling rate of the X-ray tube and the cooling rate of the tube housing as a function of the planned ambient condition.

Also, based on housing temperature profile, it is possible to temporarily modulate the ambient conditions e.g. by decreasing in room temperature or changing in the rpm of housing heat dissipation fan.

According to an embodiment of the present invention, the processing unit is configured to determine the estimated temperature profile of the X-ray anode under the planned operation condition for the upcoming imaging sequence using a digital twin model.

The exact temperature prediction model of the X-ray tube anode defined by a digital twin module that includes the physics based simulation of all influencing effects helps to have a much more precise temperature information for the anode track. This temperature cannot be measured in real-time inside a standard X-ray tube.

According to an embodiment of the present invention, the processing unit is configured to determine the estimated temperature profile of the X-ray anode under the planned operation condition for the upcoming imaging sequence using a trained machine-learning model.

According to an embodiment of the present invention, the set of scan parameters comprises one or more of a set of X-ray generator settings, a set of X-ray tube settings, a scan protocol, an anatomy of interest to be scanned, a table feed speed, and a boundary condition.

According to a second aspect of the present invention, there is provided an X-ray imaging system. The X-ray imaging system comprises an X-ray imaging device, a workflow management device, a database, a sensor arrangement, and an apparatus according to the first aspect and any associated example. The X-ray imaging device comprising an X-ray tube inside a tube housing. The workflow management device comprises information about a current operation condition of the X-ray imaging system, and information about a planned operation condition of the X-ray imaging system for the upcoming imaging sequence, wherein the planned operation condition comprises a sequence of planned scans, each planned scan being associated with a respective set of planned scan parameters. The database is configured to store information about a heat capability and a cooling rate of the X-ray anode inside the tube housing, and information about a heat capability and a cooling rate of the tube housing. The sensor arrangement comprises at least one sensor configured to monitor a current temperature profile of the tube housing usable for determining a current temperature profile of the X-ray tube. The apparatus is configured to receive data from the workflow management device, the database, and the sensor arrangement, and to provide a modified planned operation condition to the workflow management device.

According to an embodiment of the present invention, the X-ray imaging device is configured to be controlled by a control file generated by the apparatus.

According to a third aspect of the present invention, there is provided a method for managing an imaging workflow of an X-ray imaging system for an upcoming imaging sequence, the method comprising:

receiving data including (i) a current temperature profile of an X-ray anode inside a tube housing of the X-ray imaging system. (ii) information about a heat capability and a cooling rate of the X-ray anode inside the tube housing. (iii) information about a heat capability and a cooling rate of the tube housing. (iv) information about a current operation condition of the X-ray imaging system, and (v) information about a planned operation condition of the X-ray imaging system for the upcoming imaging sequence, wherein the planned operation condition comprises a sequence of planned scans, each planned scan being associated with a respective set of planned scan parameters;

determining, based on the received data, an estimated temperature profile of the X-ray anode under the planned operation condition in the upcoming imaging sequence.

comparing the estimated temperature profile of the X-ray anode with a maximum allowable hardware temperature of the X-ray anode, and in response to the determination that the estimated temperature profile is greater than or equal to the maximum allowable hardware temperature of the X-ray anode, modifying (140) the planned operation condition such that the estimated temperature profile of the X-ray anode under the modified planned operation condition is less than the maximum allowable hardware temperature of the X-ray anode, wherein the modified planned operation condition comprises a change of the sequence of planned scans and/or a change of the set of planned scan parameters of one or more planned scans; and providing the modified planned operation condition for the upcoming imaging sequence, which is preferably usable for improving the workflow of the X-ray imaging system.

The method may be at least partly computer-implemented, and may be implemented in software or in hardware, or in software and hardware. Further, the method may be carried out by computer program instructions running on means that provide data processing functions. The data processing means may be a suitable computing means, such as an electronic control module etc., which may also be a distributed computer system or a cloud computing system. The data processing means or the computer, respectively, may comprise of one or more processors, a memory, a data interface, or the like.

According to an embodiment of the present invention, the method further comprises the step of generating, based on the provided modified planned operation condition, a control file usable for controlling the X-ray imaging system.

According to another aspect of the present invention, there is provided a computer program comprising instructions to cause the device of the first aspect or the system of the second aspect to execute the steps of the method of the third aspect.

According to a further aspect of the present invention, there is provided a computer-readable medium having stored thereon the computer program.

As used herein, the term "learning" in the context of machine learning refers to the identification and training of suitable algorithms to accomplish tasks of interest. The term "learning" includes, but is not restricted to, association learning, classification learning, clustering, and numeric prediction.

As used herein, the term "machine-learning" refers to the field of the computer sciences that studies the design of computer programs able to induce patterns, regularities, or rules from past experiences to develop an appropriate response to future data, or describe the data in some meaningful way.

As used herein, the term "unit" may refer to, be part of, or include an Application Specific Integrated Circuit (ASIC), an electronic circuit, a processor (shared, dedicated, or group) and/or memory (shared, dedicated, or group) that execute one or more software or firmware programs, a combinational logical circuit, and/or other suitable components that provide the described functionality.

BRIEF DESCRIPTION OF THE DRAWINGS

These and other aspects of the invention will be apparent from and elucidated further with reference to the embodiments described by way of examples in the following description and with reference to the accompanying drawings, in which.

DETAILED DESCRIPTION OF EMBODIMENTS

X-ray imaging systems are utilized in a number of applications such as medical diagnostics, airport security, material analysis and others. For example, in a computed tomography (CT) system, an X-ray source and an X-ray detector are arranged on opposite sides of a patient. The X-ray source may generate a fan beam of X-rays. The photons of the X-ray beam will be partially absorbed by the patient's body. Thereby, bones absorb more photons as compared to lean tissue. The photons passing through the patient's body are then received by the X-ray detector, which generates a shadow image of the patient's anatomy. The resulting image is a two-dimensional projection of the three-dimensional structure of the patient's body. In a CT system, the X-ray source and the X-ray detector rotate around the patient to capture images from different viewing directions. These images can be processed by a computer system to generate a three-dimensional image of the patient's anatomy.

The X-ray source typically comprises a cathode and an anode, which are arranged inside a vacuum tube. The cathode emits electrons, which are accelerated towards the anode due to a tube voltage supplied by a power supply. With a tube voltage of for example 80 kV, electrons are accelerated from the cathode to the anode reaching a kinetic energy of 80 keV when impinging onto the anode. This energy is converted fully or partially into X-ray radiation, which may radiate through an aperture in the housing of the X-ray tube.

To produce X-ray radiation, relatively large amounts of electrical energy must be transferred to the X-ray tube. However, only a small fraction (typically less than 1%) of the energy deposited in the X-ray tube is converted into X-rays: most appears in the form of heat. This places a limitation on the use of X-ray apparatus. If excessive heat is produced in the X-ray tube, the temperature will rise above critical values, and the tube can be damaged. In order to prevent this damage, the X-ray equipment operator must be aware of the quantity of heat produced and its relationship to the heat capacity of the X-ray tube. For this reason, in case of several high power imaging scans in a sequence it might happen that the system has to cool down and the patients and staff have to wait before a next scan could be done.

In order to facilitate the imaging workflow and improve the throughput of an X-ray imaging system, an apparatus and a method are provided for managing an imaging workflow of the X-ray imaging system for an upcoming imaging sequence.

Figure 1:
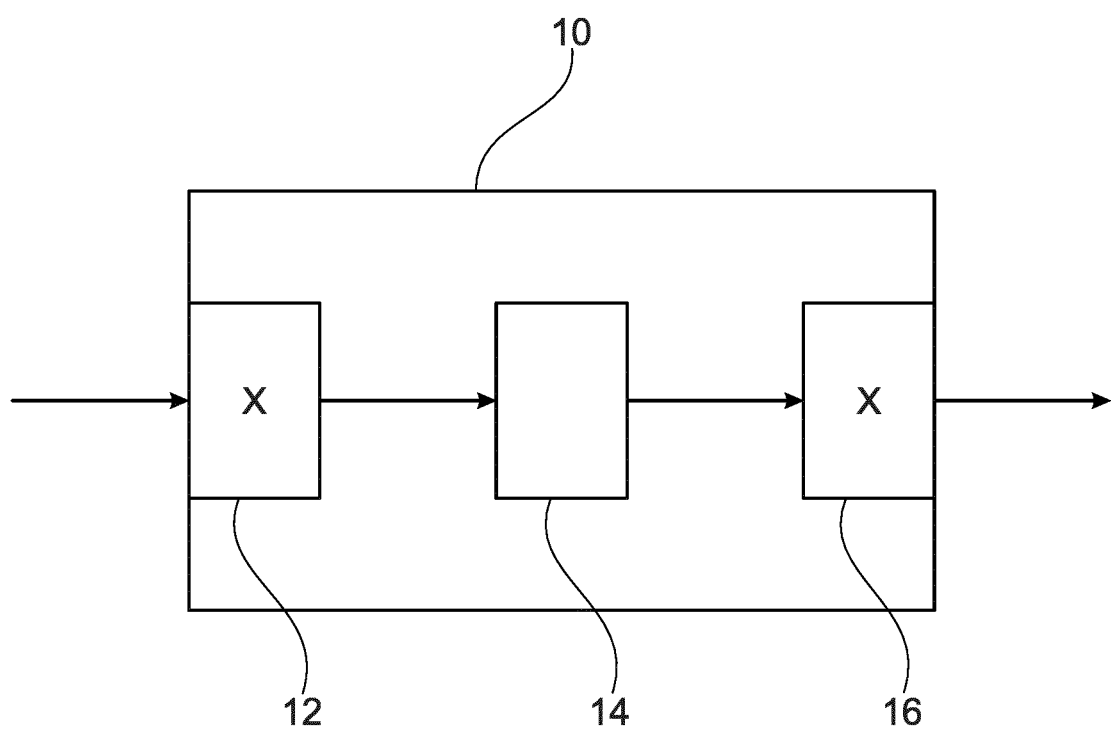
FIG. 1 illustrates an exemplary apparatus for managing an imaging workflow of an X-ray imaging system for an upcoming imaging sequence.

FIG. 1 illustrates an exemplary apparatus 10 for managing an imaging workflow of an X-ray imaging system for an upcoming imaging sequence. The exemplary apparatus 10 comprises an input unit 12, a processing unit 14, and an output unit 16.

In general, the exemplary apparatus 10 may comprise various physical and/or logical components for communicating and manipulating information, which may be implemented as hardware components (e.g., computing devices, processors, logic devices), executable computer program instructions (e.g., firmware, software) to be executed by various hardware components, or any combination thereof, as desired for a given set of design parameters or performance constraints. Although FIG. 1 may show a limited number of components by way of example, it can be appreciated that a greater or a fewer number of components may be employed for a given implementation.

In some implementations, the exemplary apparatus 10 may be embodied as, or in, a device or apparatus, such as a server, workstation, or mobile device. The exemplary apparatus 10 may comprise one or more microprocessors or computer processors, which execute appropriate software. The processing unit 14 of the exemplary apparatus 10 may be embodied by one or more of these processors. The software may have been downloaded and/or stored in a corresponding memory. e.g., a volatile memory such as RAM or a non-volatile memory such as flash, and remote memory like cloud. The software may comprise instructions configuring the one or more processors to perform the functions as described herein.

It is noted that the exemplary apparatus 10 may be implemented with or without employing a processor, and also may be implemented as a combination of dedicated hardware to perform some functions and a processor (e.g., one or more programmed microprocessors and associated circuitry) to perform other functions. For example, the functional units of the exemplary apparatus 10. e.g., the input unit 12, the one or more processing units 14, and the output unit 16 may be implemented in the device or apparatus in the form of programmable logic. e.g., as a Field-Programmable Gate Array (FPGA). In general, each functional unit of the apparatus may be implemented in the form of a circuit.

In some implementations, the exemplary apparatus 10 may also be implemented in a distributed manner. For example, some or all units of the exemplary apparatus 10 may be arranged as separate modules in a distributed architecture and connected in a suitable communication network, such as a 3rd Generation Partnership Project (3GPP) network, a Long Term Evolution (LTE) network. Internet. LAN (Local Area Network). Wireless LAN (Local Area Network). WAN (Wide Area Network), and the like.

The input unit 12 and the output unit 16 may include hardware and/or software to enable the exemplary apparatus 10 to receive a data input, and to communicate with other devices and/or a network. The input unit 12 may receive the data input via a wired connection or via a wireless connection. The output unit 16 may also provide cellular telephone communications, and/or other data communications for the exemplary apparatus 10.

The processing unit(s) 14 may execute instructions to perform the method as described herein. This will be explained hereinafter and in particular with respect to the example shown in FIG. 2.

Figure 2:
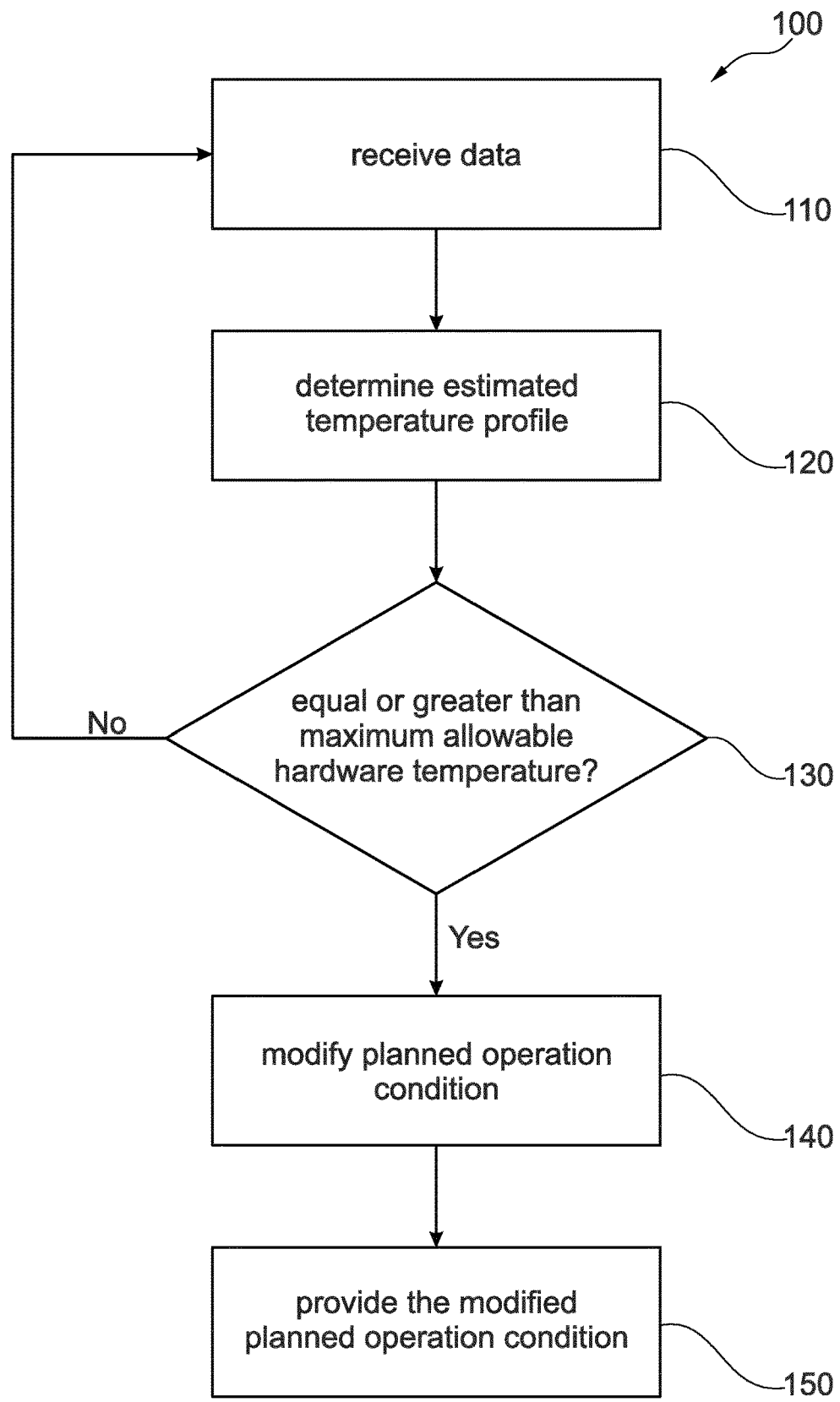
FIG. 2 illustrates a flow chart describing an exemplary method for managing an imaging workflow of an X-ray imaging system for an upcoming imaging sequence.

FIG. 2 illustrates a flow chart describing a method 100 for managing an imaging workflow of an X-ray imaging system for an upcoming imaging sequence. The method 100 may be implemented as a device, module or related component in a set of logic instructions stored in a non-transitory machine- or computer-readable storage medium such as random access memory (RAM), read only memory (ROM), programmable ROM (PROM), firmware, flash memory, etc., in configurable logic such as, for example, programmable logic arrays (PLAs), field programmable gate arrays (FPGAs), complex programmable logic devices (CPLDs), in fixed-functionality hardware logic using circuit technology such as, for example, application specific integrated circuit (ASIC), complementary metal oxide semiconductor (CMOS) or transistor-transistor logic (TTL) technology, remote memory like cloud or any combination thereof. For example, computer program code to carry out operations shown in the method 100 may be written in any combination of one or more programming languages, including an object oriented programming language such as JAVA, SMALL-TALK, C++, Python, or the like and conventional procedural programming languages, such as the "C" programming language or similar programming languages. For example, the exemplary method 100 may be implemented as the apparatus 10 shown in FIG. 1, which will be explained in detail below.

At block 110, a device, such as the apparatus 10 shown in FIG. 1, receives data via the input unit 12. The received data includes the following input parameters representing factors that affect X-ray tube heating in the upcoming sequence:
  a current temperature profile of an X-ray anode inside a tube housing of the X-ray imaging system;
  information about a heat capability and a cooling rate of the X-ray anode inside the tube housing;
  information about a heat capability and a cooling rate of the tube housing;
  information about a current operation condition of the X-ray imaging system; and
  information about a planned operation condition of the X-ray imaging system for the upcoming imaging sequence, wherein the planned operation condition comprises a sequence of planned scans, each planned scan being associated with a respective set of planned scan parameters.

The current temperature profile of the X-ray anode may be derived from sensor data. For example, the current temperature profile of the tube housing may be measured, and the current temperature profile of the X-ray anode may be derived from the temperature measurements of the tube housing. Alternatively, the current temperature profile of the X-ray anode may determined based on early history data.

The information about the heat capability of the X-ray tube may comprise heat capacities of two distinct areas, including focal spot area and anode body. The focal spot area is the point at which heat is produced within the tube. From this area, the heat moves by conduction throughout the anode body and by radiation to the tube housing. The heat capability of a given focal spot track is generally specified by the manufacturer in the form of a graph with curves on the graph showing the maximum power (KV and mA) that can be delivered to the tube for a given exposure time without producing overload. The heat capacity of the focal spot track is generally the limiting factor for single exposures. In a series of radiographic exposures. CT scanning, or fluoroscopy, the build-up of heat in the anode can become significant. The heat capacity of an anode is generally described graphically with a set of curves describing the thermal characteristics of an anode. The heating curves indicate the build-up of heat within the anode for various energy input rates. These curves apply primarily to the continuous operation of a tube, such as in CT or fluoroscopy.

The information about the cooling rate of the X-ray anode is also generally specified by the manufacture in form of a graph showing a cooling curve, which can be used to estimate the cooling time necessary between sets of exposures. The cooling rate of the X-ray anode is not constant. An anode cools faster when it has a high heat content and a high temperature. The anodes in most radiographic equipment are cooled by the natural radiation of heat to the surrounding tube enclosures. However, anodes in some high powered equipment, such as that used in CT, are cooled by the circulation of oil through the anode to a heat exchanger. Therefore, the cooling rate of the X-ray anode is dependent on the environmental condition and the cooling system.

The information about the heat capacity and cooling rate of the tube housing is also a factor that affects the X-ray tube heating. The heat capacity of the tube housing places a limitation on the extended use of the X-ray tube, rather than on individual exposures. Since the housing is generally cooled by the movement of air, or convection, its effective capacity can be increased by using forced air circulation. The information about the heat capacity and cooling rate of the tube housing may be obtained from housing heating and cooling charts supplied by the manufacturer.

The information about the current operation condition of the X-ray imaging system may include X-ray tube settings, such as mA, kV (modulation option), pulse time, focal spot size and shape, focal spot position (static or dynamic movement), and pulse pattern. The information about the current operation condition of the X-ray imaging system may include information about the anatomy of interest, such as chest/lung. Further exemplary information about the current operation condition of the X-ray imaging system may include, but is not limited to, a scan protocol, a table feed speed, and a boundary condition (e.g. full scan).

At block 120, based on the received data, an estimated temperature profile of the X-ray anode is determined under the planned operation condition in the upcoming imaging sequence. e.g. by the processing unit 14 of the apparatus 10 shown in FIG. 1.

In some examples, a digital twin model may be used to determine the estimated temperature profile of the X-ray anode under the planned operation condition for the upcoming imaging sequence. The exact temperature prediction model of the X-ray tube anode defined by the digital twin module on anode may include the physics based simulation of the influencing effects defined by the input parameters. The temperature prediction model may help to have a much more precise temperature information for the anode track. This temperature cannot be measured in real-time inside a standard X-ray tube. The simulation of the temperature under the consideration of the effects that influence the temporal performance, the spatial distribution, and the material specific parameters utilizing the digital twin model can reflect reality in a more precise way than the simple model used in the prior art.

In some examples, the processing unit 14 of the apparatus 10 may be configured to determine the estimated temperature profile of the X-ray node under the planned operation condition for the upcoming imaging sequence using a trained machine-learning model. The machine learning model has been pre-trained on historic data (e.g. temperature profile of the X-ray anode, scan protocol, imaging sequence, etc.) recorded and/or measured from previous examinations of one or more patients. Training of the machine-learning model may include the following steps of receiving the training data, applying the machine-learning model to the training data in one or more iterations. As a result of this application the pre-trained machine-learning model is then obtained, which can then be used in deployment. In deployment, new input parameters that define factors affecting heat production for the upcoming imaging sequence can be applied to the trained machine-learning model to determine the future temperature profile of the X-ray tube under the planned operation condition for the upcoming imaging sequence. For example, a neural-network model, also referred to as artificial neural networks (ANNs), may be used as an example of the machine-learning model. However, other machine learning techniques such as support vector machines, maximum likelihood, random forest, or other may be used instead of neural networks.

At block 130, the estimated temperature profile of the X-ray anode is compared with a maximum allowable hardware temperature of the X-ray anode. e.g. by the processing unit 14 of the apparatus 10 to determine whether the estimated temperature profile is greater than or equal to the maximum allowable hardware temperature of the X-ray anode. The maximum allowable hardware temperature of the X-ray anode may also be referred to as hardware temperature limitation of the X-ray anode, above which the X-ray tube will be damaged, such as melting of anode material, roughness of the focal track due to melting/re-melting of material, cracks, and other inhomogencities.

If yes, at block 140, in response to the determination that the estimated temperature profile is greater than or equal to the maximum allowable hardware temperature of the X-ray anode, the planned operation condition is modified such that the estimated temperature profile of the X-ray anode under the modified planned operation condition is less than the maximum allowable hardware temperature of the X-ray anode.

The modified planned operation condition comprises a change of the sequence of planned scans and/or a change of the set of planned scan parameters for one or more planned scans.

The change of the sequence of planned scans may include the adaption of the sequence of planned scans for patients with different anatomical thicknesses. This would mean that after a high power scan of a patient with thick anatomies it would be better to scan another patient with thinner anatomies before scanning again a patient with thick anatomies in case the tube would be close to some limits. The change of the sequence of planned scans may include the adaption of the sequence of planned scans for different anatomical regions. For example, after spiral scanning of relatively large anatomical regions (e.g. full body), it would be better to perform scanning of relative small anatomical regions (e.g. chest).

The change of the set of planned scan parameters for one or more planned scans may include the adaptation of the pulse pattern, max, kV and mA setting including modulation options. The change of the set of planned scan parameters may also include the adaption of X-ray generator settings, such as Tube specific acquisition parameters (e.g. boosting, blanking, breaking and idle times) and detection parameters (e.g. fps, integration time, etc.).

It is possible to predict possible operation combinations for the following imaging scans based on the planned parameters for the upcoming imaging sequence in an iterative process or in a non-iterative process.

In the iterative process, in response to the determination that the estimated temperature profile is greater than or equal to the maximum allowable hardware temperature of the X-ray anode, the planned operation condition may be adjusted by changing the sequence of planned scans and/or the set of planned scan parameters. Then, an updated estimated temperature profile of the X-ray anode is determined under the adjusted planned operation condition utilizing e.g. the digital twin model or trained machine learning model. The updated estimated temperature profile of the X-ray anode is then compared with the maximum allowable hardware temperature of the X-ray anode. This process may be repeated until a modified planned operation condition has an estimated temperature profile that satisfies the predefined criterion.

In the non-iterative process, multiple modified planned operation conditions may be proposed with each differing from one another in the sequence of planned scans and/or the set of planned scan parameters. The temperature profiles of the X-ray anode under all these modified planned operation conditions are determined. At least one planned operation condition satisfying the predefined criterion may be selected from the multiple modified planned operation conditions. For example, the modified planned operation condition that has a lowest value of the estimated temperature profile of the X-ray anode may be selected.

If no, the method may return to block 110 to continuously calculate the temperature during operation based on the input parameters.

At block 150, the modified planned operation condition for the upcoming imaging sequence is provided, which is preferably usable for improving the workflow of the X-ray imaging system. For example, the modified planned operation condition may be displayed or stored in a workflow managing system with information to an image processing system or an image reconstruction system.

The temperature prediction may be used as a "dynamic throughout optimizer", an "efficiency optimizer" for a system, and depending on the safety margin parameters also as a "lifetime optimizer" or any combination thereof, which will be discussed below.

Dynamic Throughout Optimizer

For example, in a hospital the standard throughput is relatively low, no high power tube with a large heat capacity/powerful cooling would be necessary. Optimization could also include reducing the peak power in exams where there is no significant associated movements and larger exposure window are permissible without degradation in image quality. In case of a special request or in case of an emergency or just with the normal growth of the number of patients the throughput limitation of the tube could be circumvented to some extend with the optimizer tool using precise temperature estimation and optimized sequence planning. This would mean that after a high power scan (e.g. a patient with thick anatomies) it would be better to scan a patient with thin anatomies before scanning again a patient with thick anatomies in case the tube would be close to some limits. In all cases, the known sequence of scans from the waiting list including the planned scan parameters are used as input for the optimizer.

Efficiency Optimizer

The planned operation condition may be modified such that the modified planned operation condition comprises a sequence of scans alternating between a high power scan and a low power scan such that a heating rate and the cooling rate of the X-ray node can be balanced to come to a substantially constant operation profile. In this way, in case an exact temperature profile could be predicted then the system could be operated in a more efficient way as high power scans and low power scans could be interfered and the heating rate and cooling rate could be balanced to come to an optimize constant operation profile. Besides a better and more efficient use of the X-ray tube also more homogenous operating conditions could lead to more precise images due to less variation. This may allow the apparatus to be used as an "efficiency optimizer".

Lifetime Optimizer

The estimated temperature profile of the X-ray anode may be compared with a predefined threshold e.g. by the processing unit 14 of the apparatus 10 shown in FIG. 1. The predefined threshold is less than the maximum allowable hardware temperature of the X-ray anode. In response to the determination that the estimated temperature profile of the X-ray anode is greater than or equal to the predefined threshold, modify the planned operation condition such that the estimated temperature profile of the X-ray anode under the modified planned operation condition is less than the predefined threshold. The difference between the predefined threshold and the maximum allowable hardware temperature of the X-ray anode defines a safety margin. As an example, the use of a larger safety margin to avoid risky high temperature scans may be used to plan for the sequence of patient scans. This feature could be very beneficial for extending the life of tube by optimizing/customizing the System EPX parameters to usage needs of the customers. In this way, the hardware (e.g. cooling) probably does not have to take care of worst case/extreme conditions, which may be also a chance for cost down and more reliable operation and lifetime. This may allow the apparatus to be used as a "lifetime optimizer".

In some examples, based on the modified planned operation condition, a control profile may be generated e.g. by the processing unit 14 of the apparatus, which is preferably for controlling the X-ray imaging system for acquiring images for the upcoming imaging sequence. This may be beneficial for an autonomous scan.

The apparatus and method as described herein may provide a real-time prediction of the temperature profile of the X-ray tube for the upcoming imaging sequence and a real-time adaption of the planned operation before operating the actual hardware.

It will be appreciated that the above operation may be performed in any suitable order, e.g., consecutively, simultaneously, or a combination thereof, subject to, where applicable, a particular order being necessitated, e.g., by input/output relations.

The apparatus and method as described herein may be applied to any imaging systems (e.g. CT, fluoroscopy, etc.) using an X-ray tube, where the exact modelling of the temperature helps to get a more precise performance information.

Figure 3:
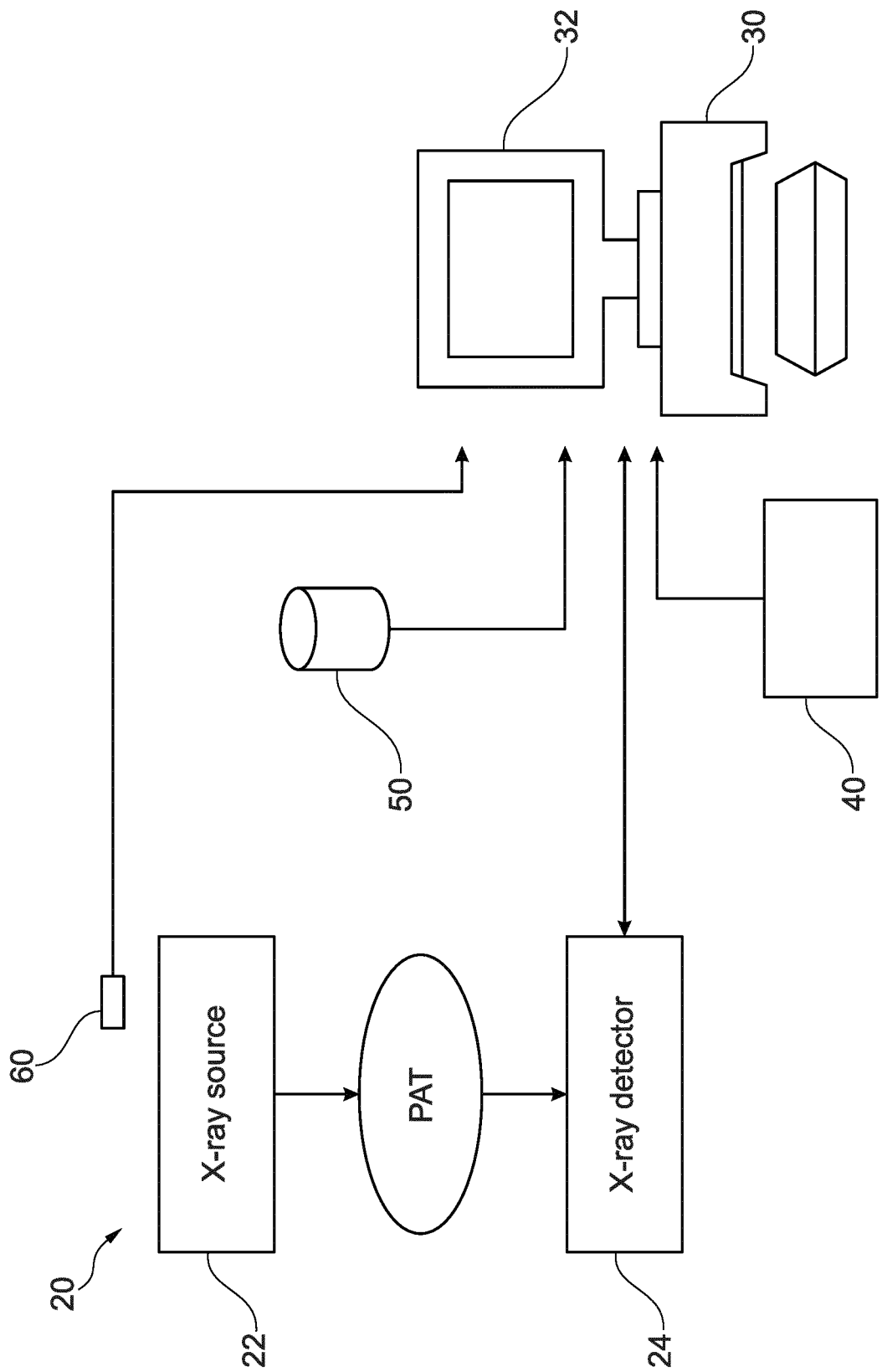
FIG. 3 illustrates an exemplary X-ray imaging system.

FIG. 3 shows schematically an exemplary X-ray imaging system 200. The exemplary X-ray imaging system 200 comprises an X-ray imaging device 20, a system console 30, a workflow management device 40, a database 50, and a sensor arrangement 60.

The X-ray imaging device 20 comprises an X-ray source 22 and an X-ray detector 24. The X-ray detector 24 is spaced from the X-ray source 22 to accommodate a patient PAT to be imaged. In some examples, the X-ray imaging device 20 may be of the C-arm type and the patient PAT may be lying on an examination table. In some examples, e.g. in a chest radiography examination, the patient PAT may stand facing a flat surface behind which is the X-ray detector 24.

In general, during an image acquisition, a collimated X-ray beam emits from the X-ray source 22, passes through the patient PAT at a region of interest (ROI), experiences attenuation by interaction with matter therein, and the attenuated beam then strikes the surface of the X-ray detector 24. The density of the organic material making up the ROI determines the level of attenuation. High-density material (such as bone) causes higher attenuation than less dense materials (such as tissue). The registered digital values for the X-ray are then consolidated into an array of digital values forming an X-ray projection image for a given acquisition time and projection direction.

Overall operation of the X-ray imaging device 20 may be controlled by an operator from the system console 30. The system console 30 may be coupled to a display 32 on which the acquired X-ray images or imager settings may be viewed or reviewed. An operator such as a medical lab technical can control via the system console 30 an image acquisition run by releasing individual X-ray exposures for example by actuating a joy stick or pedal or other suitable input means coupled to the system console 30.

In the example shown in FIG. 3, the apparatus 10 is embodied as, or in, the system console 30. For example, the apparatus 10 and its components may be resident in the system console 30 running as software routines. However, those skilled in the art will readily appreciate that the apparatus 10 may be any computing device, including desktop and laptop computers, smartphones, tablets, etc. The apparatus 10 may be a general-purpose device or a device with a dedicated unit of equipment suitable for providing the functionality as described herein. In some examples, the components of the apparatus 10 are shown as integrated in one single unit. However, in alternative examples, some or all components may be arranged as separate modules in a distributed architecture and connected in a suitable communication network. The apparatus 10 and its components may be arranged as dedicated FPGAs or as hardwired standalone chips.

The workflow management device 40 comprises information about a current operation condition of the X-ray imaging system, and information about a planned operation condition of the X-ray imaging system for the upcoming imaging sequence. The planned operation condition comprises a sequence of planned scans, each planned scan being associated with a respective set of planned scan parameters.

The database 50 is configured to store information about a heat capability and a cooling rate of the X-ray anode inside the tube housing, and information about a heat capability and a cooling rate of the tube housing. Such information is generally specified by the manufacturer.

The sensor arrangement 60 comprises at least one sensor configured to monitor a current temperature profile of the tube housing usable for determining a current temperature profile of the X-ray tube.

The apparatus 10 in form of the system console 30 is configured to receive data from the workflow management device 40, the database 50, and the sensor arrangement 60, and to provide a modified planned operation condition to the workflow management device according to the method as described herein, such as the exemplary method 100 shown in FIG. 2.

In some examples, the X-ray imaging device 20 is configured to be controlled by a control file generated by the apparatus.

In some examples, the temperature profile prediction may be further supported by the sensor arrangement 60 have a real time validation of the temperature prediction at locations where measurements could be done. However this would be not on the anode track, as that position is not accessible and temperature measurements there would not be possible with affordable costs in a product. The online monitoring and comparison of predictions and later analysis from several systems in addition allows for an optimization. For example, this may enable a closed loop of continuous and supervised learning, enabling a strategy to continually improve the machine learning model for estimating the temperature profile of the X-ray anode.

In the example of FIG. 3, only a single X-ray imaging device is illustrated. However, those skilled in the art will readily appreciate that the apparatus and method as described herein are also applicable to multiple X-ray imaging devices to achieve connected optimization. For example, in a hospital with multiple X-ray imaging devices, in case of a special request or in case of an emergency, the throughput limitation of the tube of one X-ray imaging could be circumvented to some extend with the optimizer tool by assigning patients to other X-ray imaging devices. For example, after spiral scanning of relatively large anatomical regions (e.g. full body), it would be better to use the same X-ray imaging device to perform scanning of relative small anatomical regions (e.g. chest). If a high power scan (e.g. full body) is planned in case of emergency, a different X-ray imaging device in the hospital may be determined to perform scanning of relative anatomical regions.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The invention claimed is:

1. An apparatus for managing an imaging workflow of an X-ray imaging system for an upcoming imaging sequence, comprising:
   a memory that stores a plurality of instructions; and
   at least one processor coupled to the memory and configured to execute the plurality of instructions to:
   receive data including (i) a current temperature profile of an X-ray anode inside a tube housing of the X-ray imaging system, (ii) information about a heat capability and a cooling rate of the X-ray anode, (iii) information about a heat capability and a cooling rate of the tube housing, (iv) information about a current operation condition of the X-ray imaging system, and (v) information about a planned operation condition of the X-ray imaging system for the upcoming imaging sequence, wherein the planned operation condition comprises a sequence of planned scans, each planned scan being associated with a respective set of planned scan parameters;

determine, based on the received data, an estimated temperature profile of the X-ray anode under the planned operation condition for the upcoming imaging sequence, compare the estimated temperature profile of the X-ray anode with a maximum allowable hardware temperature of the X-ray anode, in response to the determination that the estimated temperature profile is greater than or equal to the maximum allowable hardware temperature of the X-ray anode, modify the planned operation condition such that the estimated temperature profile of the X-ray anode under the modified planned operation condition is less than the maximum allowable hardware temperature of the X-ray anode, wherein the modified planned operation condition comprises a change of the sequence of planned scans and/or a change of the set of planned scan parameters for one or more planned scans; and provide the modified planned operation condition for the upcoming imaging sequence.

2. The apparatus according to claim 1, wherein the at least one processor is further configured to:

compare the estimated temperature profile of the X-ray anode with a predefined threshold, wherein the predefined threshold is less than the maximum allowable hardware temperature of the X-ray anode; and in response to the determination that the estimated temperature profile of the X-ray anode is greater than or equal to the predefined threshold, modify the planned operation condition such that the estimated temperature profile of the X-ray anode under the modified planned operation condition is less than the predefined threshold.

3. The apparatus according to claim 1, wherein the at least one processor is configured to:

modify the planned operation condition to provide a plurality of candidate planned operation conditions, each candidate planned operation condition differing from another in the set of planned scan parameters and/or the sequence of planned scans;

determine, under each candidate planned operation condition, a respective estimated temperature profile of the X-ray anode; and select a candidate planned operation condition that has a lowest value of the estimated temperature profile of the X-ray anode.

4. The apparatus according to claim 1, wherein the modified planned operation condition comprises a sequence of scans alternating between a high power scan and a low power scan such that a heating rate and the cooling rate of the X-ray node can be balanced to come to a substantially constant operation profile.

5. The apparatus according to claim 1, wherein the apparatus is configured to generate, based on the modified planned operation condition, a control file usable for controlling the X-ray imaging system.

6. The apparatus according to claim 1, wherein the at least one processor is further configured to receive a planned ambient condition for the upcoming imaging sequence; and wherein the at least one processor is configured to determine the cooling rate of the X-ray tube and the cooling rate of the tube housing as a function of the planned ambient condition.

7. The apparatus according to claim 1, wherein the at least one processor is configured to determine the estimated temperature profile of the X-ray anode under the planned operation condition for the upcoming imaging sequence using a digital twin model.

8. The apparatus according to claim 1, wherein the at least one processor is configured to determine the estimated temperature profile of the X-ray anode under the planned operation condition for the upcoming imaging sequence using a trained machine-learning model.

9. The apparatus according to claim 1, wherein the set of scan parameters comprises one or more of:

a set of X-ray generator settings;
a set of X-ray tube settings;
a scan protocol;
an anatomy of interest to be scanned;
a table feed speed; and
a boundary condition.

10. An X-ray imaging system, comprising:

an X-ray imaging device comprising an X-ray tube inside a tube housing; and an apparatus for managing an imaging workflow of the X-ray imaging device for an upcoming imaging sequence, wherein the apparatus is configured to:

receive data including (i) a current temperature profile of an X-ray anode inside a tube housing of the X-ray imaging system, (ii) information about a heat capability and a cooling rate of the X-ray anode, (iii) information about a heat capability and a cooling rate of the tube housing, (iv) information about a current operation condition of the X-ray imaging system, and (v) information about a planned operation condition of the X-ray imaging system for the upcoming imaging sequence, wherein the planned operation condition comprises a sequence of planned scans, each planned scan being associated with a respective set of planned scan parameters;

determine, based on the received data, an estimated temperature profile of the X-ray anode under the planned operation condition for the upcoming imaging sequence, compare the estimated temperature profile of the X-ray anode with a maximum allowable hardware temperature of the X-ray anode;

in response to the determination that the estimated temperature profile is greater than or equal to the maximum allowable hardware temperature of the X-ray anode, modify the planned operation condition such that the estimated temperature profile of the X-ray anode under the modified planned operation condition is less than the maximum allowable hardware temperature of the X-ray anode, wherein the modified planned operation condition comprises a change of the sequence of planned scans and/or a change of the set of planned scan parameters for one or more planned scans; and provide the modified planned operation condition for the upcoming imaging sequence.

11. The X-ray imaging system according to claim 10, wherein the X-ray imaging device is configured to be controlled by a control file generated by the apparatus.

12. A method for managing an imaging workflow of an X-ray imaging system for an upcoming imaging sequence, the method comprising:

receiving data including (i) a current temperature profile of an X-ray anode inside a tube housing of the X-ray imaging system, (ii) information about a heat capability and a cooling rate of the X-ray anode inside the tube housing, (iii) information about a heat capability and a cooling rate of the tube housing, (iv) information about a current operation condition of the X-ray imaging system, and (v) information about a planned operation condition of the X-ray imaging system for the upcoming imaging sequence, wherein the planned operation condition comprises a sequence of planned scans, each planned scan being associated with a respective set of planned scan parameters;

determining, based on the received data, an estimated temperature profile of the X-ray anode under the planned operation condition in the upcoming imaging sequence, comparing the estimated temperature profile of the X-ray anode with a maximum allowable hardware temperature of the X-ray anode, and in response to the determination that the estimated temperature profile is greater than or equal to the maximum allowable hardware temperature of the X-ray anode, modifying the planned operation condition such that the estimated temperature profile of the X-ray anode under the modified planned operation condition is less than the maximum allowable hardware temperature of the X-ray anode, wherein the modified planned operation condition comprises a change of the sequence of planned scans and/or a change of the set of planned scan parameters of one or more planned scans; and providing the modified planned operation condition for the upcoming imaging sequence, which is preferably usable for improving the workflow of the X-ray imaging system.

13. The method according to claim 12, further comprising:

generating, based on the provided modified planned operation condition, a control file usable for controlling the X-ray imaging system.

14. A non-transitory computer-readable medium for storing executable instructions that, when executed, cause a method of claim 12 to be performed.

* * * * *